United States Patent
Bergh et al.

(10) Patent No.: US 10,984,675 B2
(45) Date of Patent: *Apr. 20, 2021

(54) MOTION TRAINING AID WITH STIMULATOR

(71) Applicant: West & Bergh IT Consulting AB, Höllviken (SE)

(72) Inventors: Christian Bergh, Höllviken (SE); Ulf Bering, Ramlösa (SE); Markus Westerberg, Höllviken (SE)

(73) Assignee: WEST & BERGH HOLDING AB

( * ) Notice: Subject to any disclaimer, the term of this patent is extended or adjusted under 35 U.S.C. 154(b) by 225 days.

This patent is subject to a terminal disclaimer.

(21) Appl. No.: 15/757,808

(22) PCT Filed: Jun. 2, 2017

(86) PCT No.: PCT/EP2017/063501
§ 371 (c)(1),
(2) Date: Mar. 6, 2018

(87) PCT Pub. No.: WO2017/207774
PCT Pub. Date: Dec. 7, 2017

(65) Prior Publication Data
US 2020/0234608 A1    Jul. 23, 2020

(30) Foreign Application Priority Data

Jun. 3, 2016 (EP) ..................... 16172929

(51) Int. Cl.
*G09B 19/00* (2006.01)
*A61M 21/00* (2006.01)
*A61N 1/36* (2006.01)

(52) U.S. Cl.
CPC ......... *G09B 19/0038* (2013.01); *A61M 21/00* (2013.01); *A61M 2021/0072* (2013.01);
(Continued)

(58) Field of Classification Search
CPC ............. G09B 19/0038; A61M 21/00; A61M 2021/0072; A61M 2205/3317; A61M 2230/63; A61N 1/36031; A61N 1/36034
(Continued)

(56) References Cited

U.S. PATENT DOCUMENTS 6,096,062 A    8/2000  Silvian
9,173,596 B1  11/2015  Berme et al.
(Continued)

FOREIGN PATENT DOCUMENTS

GB    2462780 A    2/2010
WO  2014153201 A1   9/2014

OTHER PUBLICATIONS

International Search Report for corresponding International application No. PCT/EP2017/063501, dated Sep. 28, 2017.
(Continued)

*Primary Examiner* — Robert P Bullington
(74) *Attorney, Agent, or Firm* — Tarolli, Sundheim, Covell & Tummino LLP

(57) ABSTRACT

A training aid stimulator for providing fast perceptive feedback is provided. The training aid stimulator includes a first skin electrode for making electrical contact to the body of a user and a second skin electrode for making electrical contact to the body of a user. A body capacitance charging module is connected to the first skin electrode and a discharge module is connected to the second skin electrode for a feedback discharging of a body capacitance. A processor is connected to the body capacitance charging module for controlling the charging of a body capacitance to a predetermined first voltage level, wherein the processor is connected to the discharge module for controlling a feedback discharge of the body capacitance. The stimulator further
(Continued)

comprises a measurement module for measuring the level of charge of the body capacitance.

3 Claims, 4 Drawing Sheets

(52) U.S. Cl.
CPC . *A61M 2205/3317* (2013.01); *A61M 2230/63* (2013.01); *A61N 1/36031* (2017.08); *A61N 1/36034* (2017.08)

(58) Field of Classification Search
USPC .......................................................... 434/247
See application file for complete search history.

(56) References Cited

U.S. PATENT DOCUMENTS

| | | |
|---|---|---|
| 2004/0064157 A1 | 4/2004 | Norton |
| 2013/0089843 A1 | 4/2013 | Hutchison |
| 2014/0199672 A1 | 7/2014 | Davidson |
| 2014/0343625 A1* | 11/2014 | O Laighin ......... A61N 1/36125 607/48 |
| 2015/0018111 A1 | 1/2015 | Nadkarni et al. |

OTHER PUBLICATIONS

European Search Report corresponding to European Patent Application No. 16 172 927.2 dated Apr. 25, 2019.

* cited by examiner

MOTION TRAINING AID WITH STIMULATOR

RELATED APPLICATIONS

The present invention is a U.S. National Stage under 35 USC 371 patent application, claiming priority to Serial No. PCT/EP2017/063501, filed on 2 Jun. 2017; which claims priority of EP 16172929.8, filed on 3 Jun. 2016, the entirety of both of which are incorporated herein by reference.

TECHNICAL FIELD

The present invention relates to the field of training aids, i.e., devices that helps a person or animal better perform some activity of that person or animal. More particularly the present invention relates to motion training aids, i.e., systems or devices that provide some kind of feedback relating to a motion performed by the user. Even more particularly it relates to sports movements training aids.

PRIOR ART

One example of motion training aid is known from WO2003024544. It discloses a repetitive motion feedback system is provided with various sensors and devices for monitoring aspects of a repetitive motion sequence, such as a golf swing. The monitored aspects can include motion properties of an object moved by the user, position properties of the user and motion properties of the user. A data processing system for receiving data of the monitored aspects provides feedback data that is provided to a feedback output device, such as a graphical display device or speaker, so that the user is provided with feedback regarding the repetitive motion sequence. In one particular embodiment, the user's performance is compared to a template of a prior performance, with feedback being provided regarding the differences.

Another prior art document is U.S. Pat. No. 6,778,866 disclosing a method and apparatus for teaching a person how to perform a specific body motion in a consistent manner is based on electronically measuring one or more parameters of an actual body motion, comparing the one or more measured parameters with corresponding parameters of a target body motion, and providing a sensible feedback to the user based on a degree of correspondence between the one or more measured parameters and the corresponding target parameters. In a particular embodiment, the feedback is audible. More specifically the feedback is a musical tune that has a particular characteristic (such as rhythm) that is particularly suited to a particular body motion (such as a golf swing). The feedback may be in the form of electronically causing the musical tune to go off-key in proportion to a discrepancy between the actual body motion and the target body motion.

A further prior art system and method for teaching ergonomic motion of an athlete, for example a golfer is disclosed in WO200518759. The system including the video camera for capturing successive image of the golfer executing a preferring golf swing and a threshold definition system that allows the golfer define a spatial region of the video image. If the spatial region is intruded upon, an alarm is actuated, thereby providing feedback so the golfer may alter the technique of the next attempted motion. For example, the golfer may define the region such that if the club moves off plane during a swing, a tee removal system causes the ball to disappear. In this manner, the golfer is only able to hit the ball when the club stays on plane.

SUMMARY OF THE INVENTION

The inventors are aiming at providing a device for providing fast feedback for training devices used to train and perfect some kind of user behaviour, or action, wherein this behaviour or action is happening relatively quickly. Examples of such behaviours or actions include but are not limited to e.g. sports motions, such as technically complex motions occurring in e.g. athletic field events (high jump, pole vault, hammer throw, javelin throw etc), or gymnastics (jumps, choreography, cheerleading moves), or baseball, or golf (golf swing, putting stroke), just to mention a few.

It is desirable that a feedback signal signalling a less efficient move, or a "bad" move, or a movement that deviates from a reference movement should be instantaneous, or at least perceived as instantaneous by the user. The stimulus unit is configured to deliver the stimulus with very short delay, preferably, less than 50 ms, or more preferred less than 20 ms, or most preferred less than 10 ms. The stimulus should also be distinct. The inventors are aiming at providing a noticeable and distinct feedback in order to indicate and point out an undesirable motion to discourage said undesirable motion by the user.

In various embodiments the stimulus unit comprises a body capacitance charging module and a discharge module with body electrodes. The body capacitance charging module is charged to a level that is sufficient to cause an electric shock to the person or animal performing the activity. The electric shock is caused when there is a disagreement between the position values of the current motion and of the predetermined desired motion. The level of charge or the voltage of the body capacitance charging module is measured and further charge is supplied when necessary to maintain a level that is sufficient to provide the electric shock.

BRIEF DESCRIPTION OF THE DRAWINGS

In order that the manner in which the above recited and other advantages and objects of the invention are obtained will be readily understood, a more particular description of the invention briefly described above will be rendered by reference to specific embodiments thereof which are illustrated in the appended drawings.

Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

Definitions

Figure 1:
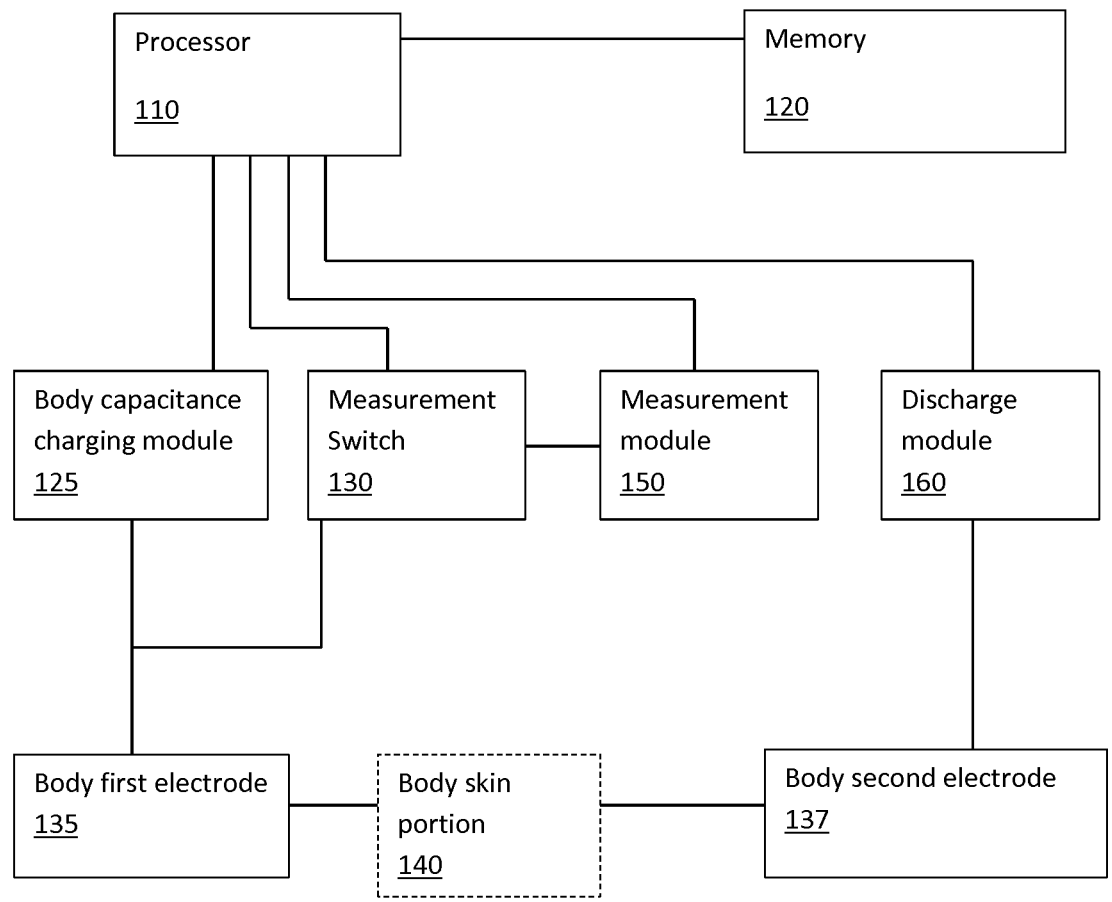
FIG. 1 is a block diagram of a stimulator device according to an embodiment of the present invention.

For the purpose of the present invention, and in the following text, the following terms are used with the meaning as explained below.

"Motion representation": A "motion representation" is a usually mathematical representation of a motion. The motion representation may include representations of linear and rotational motion position, motion velocity, and motion acceleration. For example, the motion may be represented by the current position of a predetermined point on the body of a user, or the motion may be represented by a (motion) track, see below.

"Position": With the term "position", as used herein is understood the physical local position of a sensor unit or small object in relation to a nearby reference point, and expressed using a suitable coordinate system. Typically, in the context of the present invention, positions are within the magnitude of 0-5 meters from the reference point.

"Undesired motion": The term "undesired motion" is used to denote a motion that is undesired or comprises an undesired feature as seen from the point of view of the user, and/or his or her coach.

"Body motion tracker": As used herein, the term "body motion tracker" denotes a device or a system, or a piece of computer code when executed capable of tracking one or more predefined points of a user's body over time, based on processed sensor data.

"Tracking": With the term "tracking" is understood the activity of collecting and storing (recording) consecutive positions of one or more predefined points on a user's body during a motion.

"Motion track": With the term "motion track" is meant the result of the tracking activity, i.e., the collective amount of stored consecutive positions of a predefined body point over time, starting at a start point or start time, and ending at a finishing point or finishing time.

"Reference motion track": A "reference motion track" is a desired motion track that can be used to create a model to which motion representations of motions can be compared.

"Rotation angle" or "Angle of rotation": In two dimensional space the "angle of rotation" is a measurement of the amount, the angle, by which an object is rotated about a fixed point. In three-dimensional space rotation is measured and indicated using angles of rotation about three coordinate axes.

"Predefined body point": With the term "predefined body point" is meant a point on a user's body that has been provided with means for facilitating the tracking of said point, e.g. a sensor unit.

"Attitude": In the context of the present invention the term "attitude" is used to denote an object's orientation (attitude, angular position) in space. The attitude may be represented by pitch, yaw and roll angles or, alternatively, by an attitude vector or axis, and a rotation angle around that vector or axis, i.e. axis-angle representation, c.f. Euler's rotation theorem.

"Motion sensor unit": A "motion sensor unit" is understood to be a unit, attachable to a user's body, that are able to deliver motion information, such as accelerations, information making it possible to determine the sensor's attitude and three-dimensional position or changes in the same position during a motion of the user, in a suitable reference system. The sensor unit is conceived to be small and lightweight enough not to interfere with the motion of the user.

"Control unit": In the context of the present invention a "control unit" is a unit comprising a man-machine interface for operating a device, it also usually comprises wireless communication means to communicate with the processor and/or the motion sensor unit.

"Sample": In the context of the present invention the term "sample" is used to denote a calculated state of the motion sensor unit at a particular moment in time, and may include representations of linear and/or rotational: motion position, motion velocity, and motion acceleration as calculated by the processor based on motion sensor data from the motion sensor unit and also based on a reference frame, i.e., a coordinate system. Associated with the sample is a sample number and/or a sample time.

"Processor": In the context of the present invention the term "processor" is used to denote a processor system irrespective if it comprises one or more logical or physical processors, if nothing else is explicitly mentioned.

"Memory": In the context of the present invention the term "memory" is used to denote a memory system irrespective if it comprises one or more logical or physical memories, if nothing else is explicitly mentioned "Stimulator": In the context of the present invention the term stimulator is used to denote a device, attachable to a body of a person or animal, and upon receiving a command, capable of eliciting a stimulus perceptible by that person or animal.

"Motion": With the term "motion" is understood any body movement performed by a person, composite or simple, may it be a movement of one or more of his or her extremities, or torso, or centre of gravity. Any possible ambiguities should be solved by the context in which the term is used. The term is also used to denote the movement as sensed by a sensor. Example motions include portions of or complete high jump, pole vault, hammer throw, javelin throw, gymnastics jumps, choreography moves, cheerleading moves, baseball batting, baseball pitching, golf swing, putting stroke.

The stimulus unit is configured to deliver the stimulus with very short delay, preferably, less than 50 ms, or more preferred less than 20 ms, or most preferred less than 10 ms. The stimulus should also be distinct.

In order to be able to deliver the stimulus, i.e., an electric discharge, with short notice, there is provided a training aid stimulator device as outlined in FIG. 1. The block diagram in FIG. 1 shows a stimulator device according to an embodiment of the present invention. A processor 110 is connected to a memory 120. Further, the processor is connected to a body capacitance charging module 125 for charging a body capacitance connected via a first body electrode 135. Further the processor 110 is connected to a measurement switch 130. The measurement switch is controlled by the processor to connect and disconnect a measurement module 150 to the first body electrode 135 at certain times. The timing of the connecting and disconnecting respectively of the measurement module to the first body electrode 135 will be further explained below. The processor 110 is further connected to a discharge module 160 in order to control the delivery of a discharge of a body capacitance connected via the first body electrode 135 and a second body electrode 137.

Figure 2:
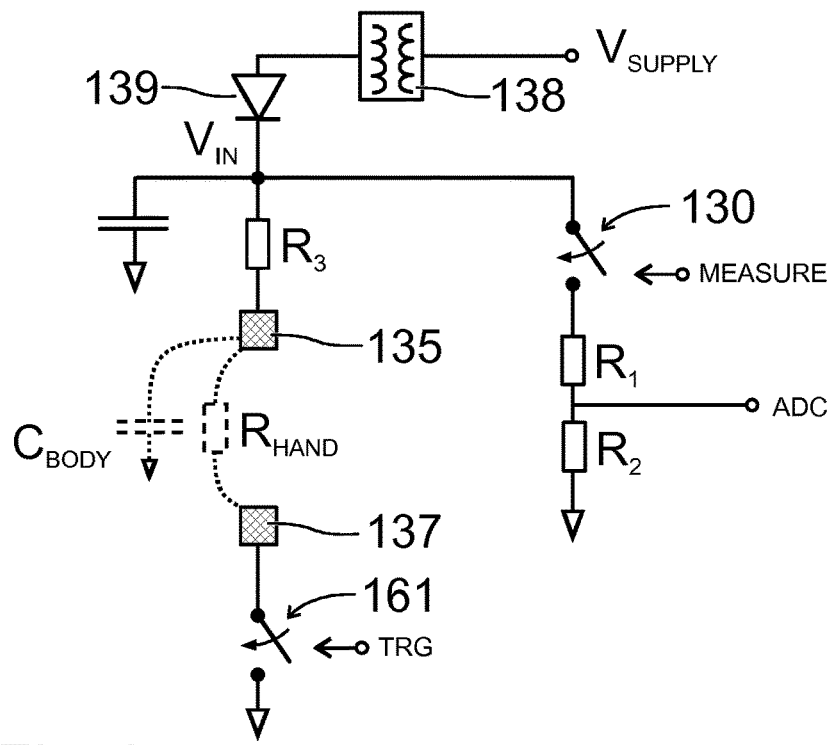
FIG. 2 shows a principal circuit diagram of a basic embodiment of a stimulator device.
Figure 3:
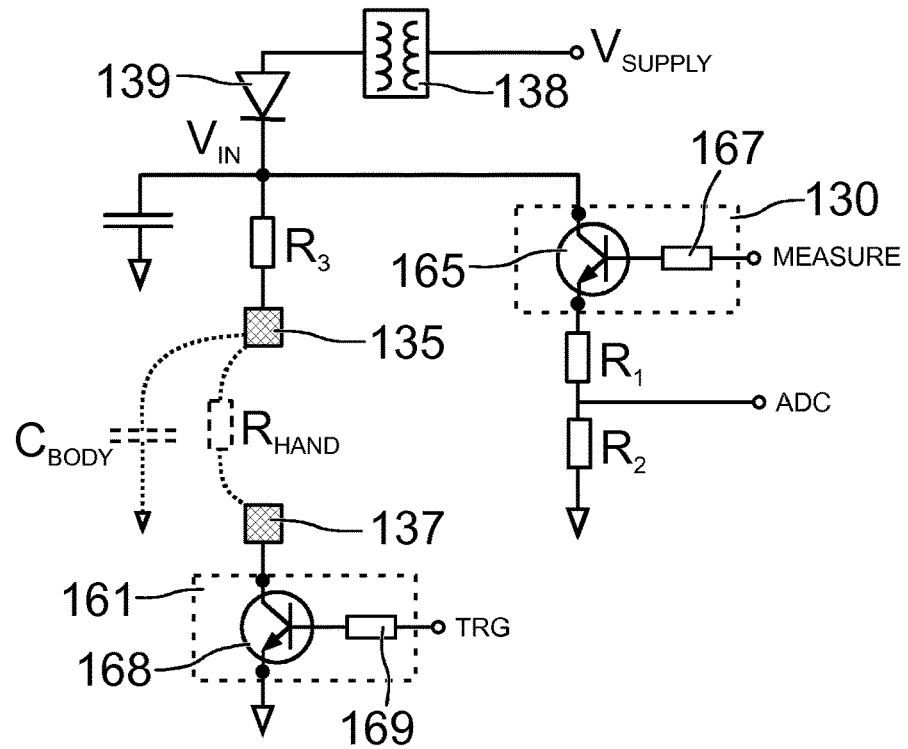
FIG. 3 shows principal circuit diagram of second embodiment of a stimulator device.

FIG. 2 and FIG. 3 show alternate principal wiring diagrams for a first circuit, and a second circuit capable of providing a distinct biofeedback electrical stimulus to the skin of a user. FIG. 2 shows a stimulator circuit comprising a first electrode 135 and a second electrode 137 devised to make contact to the skin of a user. Said first and said second electrodes can also be referred to as skin electrodes. Power at a low voltage level is supplied at $V_{SUPPLY}$. The low voltage normally is DC (Direct Current) supplied by a battery which is stepped up in a transformer device 138 to a higher level, $V_{IN}$. In various embodiments the transformer device 138 comprises a DC-to-DC converter or an electric power converter. A measuring switch 130 is connected between $V_{IN}$ and a first resistor $R_1$ of a voltage divider. The voltage divider is made up of the first resistor $R_1$ and a second resistor $R_2$. An analog to digital converter ADC is connected between the resistors $R_1$ and $R_2$ and could be said to constitute a measurement module 150 together with these resistors. The measuring switch 130 is connected to and controlled by a signal MEASURE from the processor 110. An electrical model for the stimulator circuit as attached to the human skin has been devised. The model includes a capacitance of the body, $C_{BODY}$, and a resistance $R_{HAND}$ of the skin between said first electrode 135 and said second electrode 137.

The stimulator circuit further comprises a discharge switch 161 for controlling a feedback discharge also called a biofeedback electrical stimulus. The discharge switch 161 is connected between the second skin electrode 137 and earth to provide a discharge drain when triggered by a trigger signal from trigger output, TRG, of the processor. When a voltage is applied at $V_{SUPPLY}$ and increased in the transformer device 138 the capacitance of the body, $C_{BODY}$, will be charged to a predetermined level. The actual level is measured by applying the signal MEASURE and reading a voltage signal in the voltage divider at ADC. An analog to digital converter can be used to provide the processor 110 with the actual reading of voltage level. When the predetermined level is reached the processor 110 is ready to provide a signal at TRG to open the discharge switch 161. As a result the capacitance $C_{BODY}$ is discharged and a pulse is experienced by the person carrying said first electrode 135 and said second electrode 137.

Figure 4:
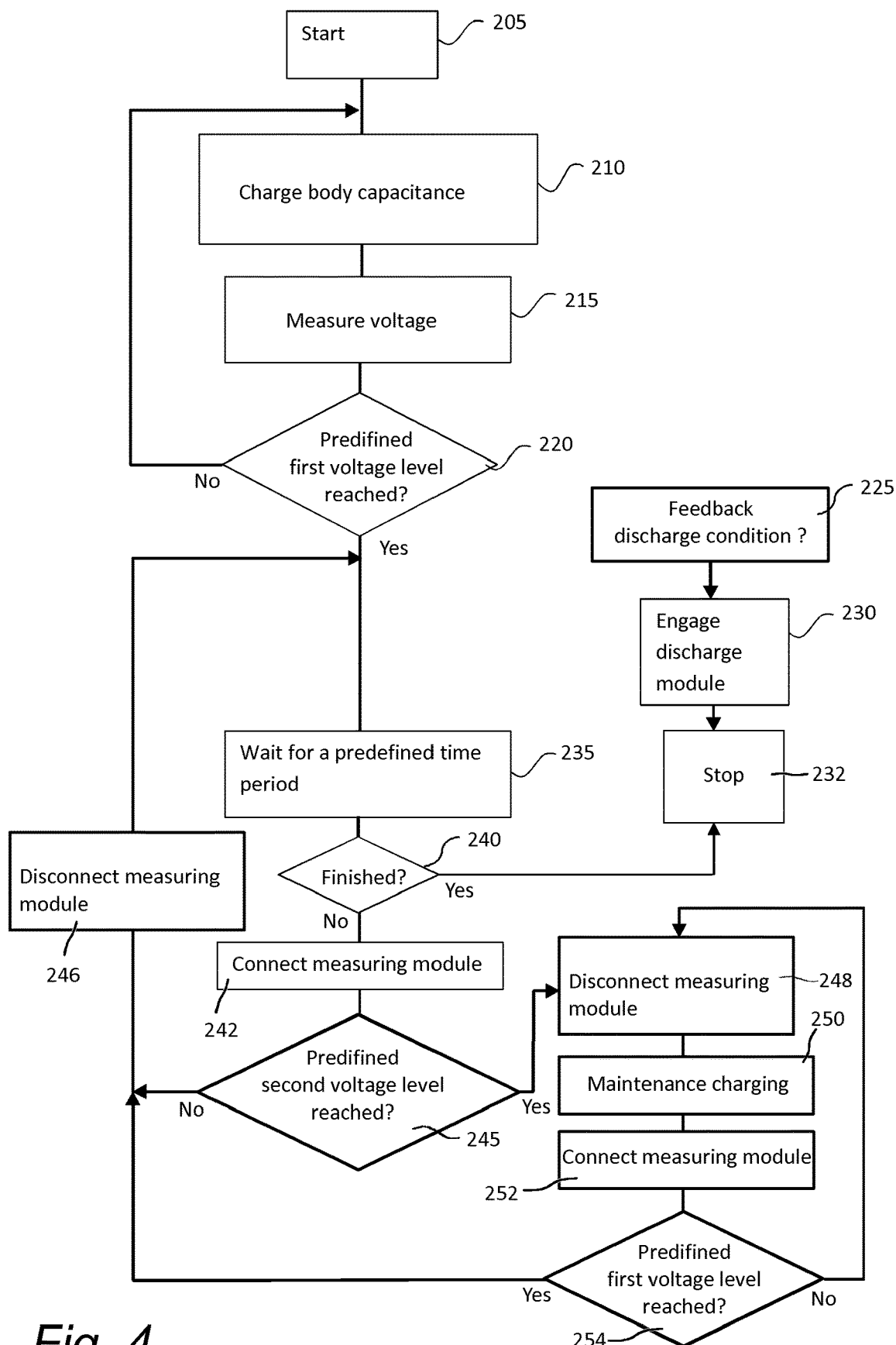
FIG. 4 is a flowchart over method steps performed by the device of FIG. 1.

The TRG signal is delayed until a specific condition is present. A continuous discharge through first resistor $R_1$ and second resistor $R_2$ is avoided in the embodiment shown in FIG. 2 by opening the measuring switch 130. In the embodiment shown in FIG. 3 an implementation of the measuring switch 130 comprises a first transistor 165 connected at a control input to a first control resistor 167 receiving the MEASURE signal. In a similar way the discharge switch 161 comprises a second transistor 168 connected at a control input to a second control resistor 169 provided for receiving the TRG signal from the processor. Still, there will be some minor continuous discharging from $C_{BODY}$, but by a maintenance or support charging as described below with reference to FIG. 4 and FIG. 5 this problem can be avoided.

The process of maintenance charging (support charging or top-up charging) is started in block 205 and the charging is started in block 210. The processor 110 then applies signal MEASURE to the measuring switch and the voltage over second resistor $R_2$ is measured in block 215. In block 220 it is checked whether a predefined first voltage level is reached. If the predefined first voltage level is not reached the charging in block 210 continues. If the predefined first voltage level is reached the processor continuously awaits a condition for a feedback discharge in block 225. When a condition for discharge is at hand the discharge module 160 is activated in block 230. The device then is stopped in block 232. If there is no condition for discharge the processor enters a wait condition for a predetermined time period in block 235.

Figure 5:
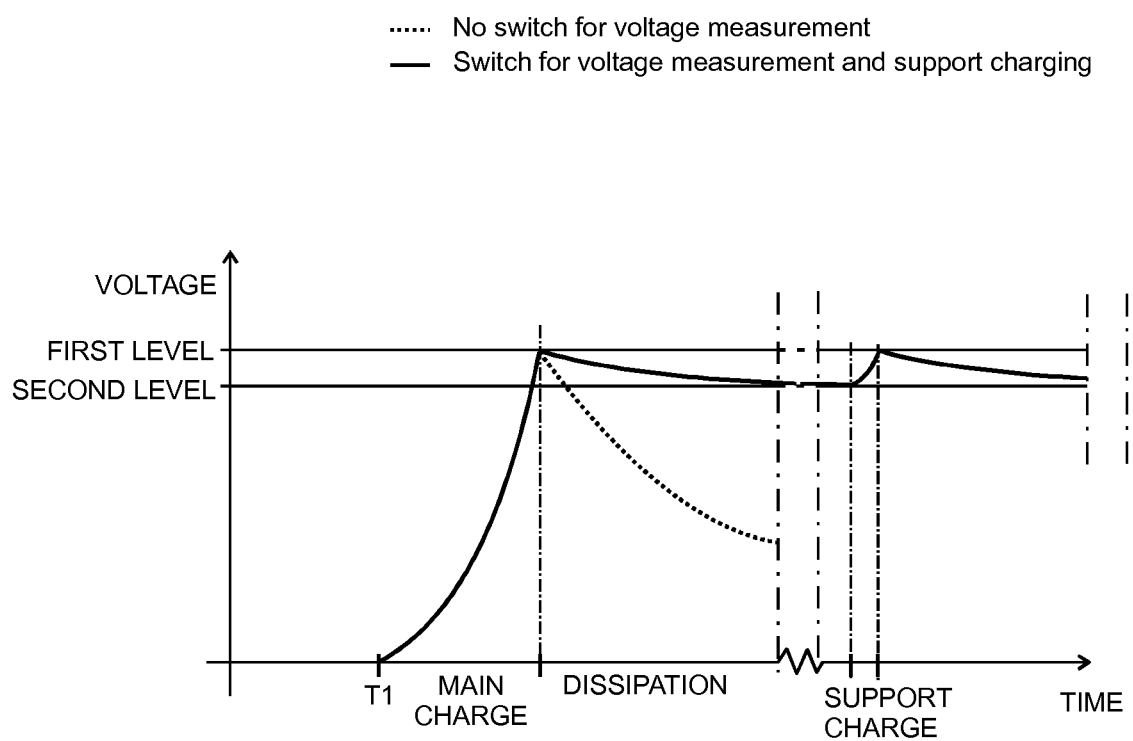
FIG. 5 is a diagram showing a charging process used in a stimulator device according to an embodiment of the present invention.

The processor then checks if the full process is finished in block 240. If the process is finished, the charge of the body capacitance is slowly dissipated, and the device then is stopped in block 232. If the process is still in operation (motion continues) the measurement module 150 is activated in block 242 and it is checked in block 245 whether voltage of voltage divider $R_1$, $R_2$ has dropped to or below a predetermined second level, c.f. FIG. 5. If voltage has not dropped to or below said predetermined second level the measuring module is switched off in block 246 and the process returns to block 235.

If voltage has dropped to or below said predetermined second level the measuring module is switched off in block 248 to preserve charge. Then maintenance charging is activated in block 250. The maintenance charging is maintained for a predetermined time period after which the measurement module 150 is activated in block 252. In block 254 it is checked whether the predefined first voltage level is reached. If the predefined first voltage level is not reached the measuring module is disconnected in block 248 and the maintenance charging in block 250 continues. If the predefined first voltage level is reached the measuring module is disconnected in block 246 and the process returns to block 235.

The diagram of FIG. 5 shows the charging and maintenance charging processes described above with reference to FIG. 4. A main charge process corresponding to the charge block 210 is initiated at time T1. When the predetermined first voltage level is reached a discharge process starts. The dotted line indicates the discharge that would take place, should the measurement switch 130 be omitted. The voltage level in that case soon would reach a level where a controlled discharge would not be sensed by the user in the intended way. As a result of the measurement module 150 measuring a low voltage level, a support or maintenance charging instead will be initiated when the voltage level drops to or below the second level. As soon as the first voltage level is reached again the charging is stopped. The voltage drop between the first level and the second level is at a level that will not impair the feedback discharge. The support or maintenance charging will be initiated repeatedly when the voltage level reaches the second level.

While certain illustrative embodiments of the invention have been described in particularity, it will be understood that various other modifications will be readily apparent to those skilled in the art without departing from the scope and spirit of the invention. Accordingly, it is not intended that the scope of the claims appended hereto be limited to the description set forth herein but rather that the claims be construed as encompassing all equivalents of the present invention which are apparent to those skilled in the art to which the invention pertains.

LEGEND

100 Stimulator
110 Processor
120 Memory
125 Body capacitance charging module
138 Transformer device
130 Measurement switch
135 First skin electrode
137 Second skin electrode
150 Measurement module 152 Analog to digital converter
160 Discharge module
161 Discharge switch
165 First transistor (Measurement switch)
167 First control resistor (Measurement switch)
168 Second transistor (Discharge switch)
169 Second control resistor (Discharge switch)
R1, R2 etc Resistances

The invention claimed is:

1. A biofeedback stimulator comprising:
a first skin electrode for making electrical contact to a body of a user;
a second skin electrode for making electrical contact to the body of the user;
a body capacitance charging module connected to the first skin electrode;
a discharge module connected to the second skin electrode for a feedback discharging of a body capacitance charged by the body capacitance charging module; and
a processor connected to the body capacitance charging module for controlling the charging of the body capacitance to a predetermined first voltage level,
wherein the processor further being connected to the discharge module for controlling a feedback discharge of the body capacitance through the skin via the first skin electrode and the second skin electrode,
wherein the biofeedback stimulator further comprises a measurement module for measuring a level of charge of the body capacitance, and
wherein the processor is configured for keeping the biofeedback stimulator ready to discharge by repeatedly measuring the level of charge of the body capacitance and by providing a maintenance charging by activating the body capacitance charging module when voltage of the body capacitance is at or below a predetermined second voltage level.

2. The biofeedback stimulator according to claim 1, further comprising a measurement switch for connecting and disconnecting the measurement module, wherein the processor is further configured to repeatedly switch on and switch off the measurement switch.

3. A method for keeping a biofeedback stimulator prepared to deliver a biofeedback electrical stimulus to the body of a user via electrodes, the method comprising:
applying a charging voltage to the electrodes;
measuring, using a measurement module, a voltage over the electrodes, the voltage corresponding to a charging level;
disconnecting the measurement module when a first voltage level is reached;
waiting a predetermined period of time; and
re-connecting the measurement module, and providing maintenance charging if a measured voltage level is at or below a second voltage level.

* * * * *